United States Patent
Weisman et al.

(10) Patent No.: US 8,591,434 B2
(45) Date of Patent: Nov. 26, 2013

(54) FILTER FOR FINE NEEDLE BIOPSY

(75) Inventors: Michal Weisman, Fair Lawn, NJ (US); Shawn Ryan, Upton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 422 days.

(21) Appl. No.: 12/871,003

(22) Filed: Aug. 30, 2010

(65) Prior Publication Data

US 2011/0066074 A1 Mar. 17, 2011

Related U.S. Application Data

(60) Provisional application No. 61/241,677, filed on Sep. 11, 2009.

(51) Int. Cl.
*A61B 5/00* (2006.01)
(52) U.S. Cl.
USPC .................................................. 600/566
(58) Field of Classification Search
USPC ............................................... 600/564–567
See application file for complete search history.

(56) References Cited

U.S. PATENT DOCUMENTS

| | | | | |
|---|---|---|---|---|
| 4,986,278 A | * | 1/1991 | Ravid et al. | 600/566 |
| 5,275,609 A | * | 1/1994 | Pingleton et al. | 606/170 |
| 5,964,716 A | * | 10/1999 | Gregoire et al. | 600/564 |
| 7,066,893 B2 | * | 6/2006 | Hibner et al. | 600/566 |
| 7,510,535 B2 | * | 3/2009 | Hibner et al. | 600/566 |
| 7,517,321 B2 | * | 4/2009 | McCullough et al. | 600/566 |
| 7,918,803 B2 | * | 4/2011 | Ritchart et al. | 600/566 |
| 8,231,544 B2 | * | 7/2012 | Mark | 600/566 |

FOREIGN PATENT DOCUMENTS

| | | |
|---|---|---|
| EP | 1 293 167 | 3/2003 |
| EP | 1 832 235 | 9/2007 |
| WO | 02/062231 | 8/2002 |
| WO | 04/000126 | 12/2003 |
| WO | 2007/110812 | 10/2007 |

\* cited by examiner

*Primary Examiner* — Max Hindenburg
(74) *Attorney, Agent, or Firm* — Fay Kaplun & Marcin, LLP

(57) ABSTRACT

A biopsy needle comprises a first lumen open to a tissue penetrating distal tip of the needle for receiving a tissue sample therein and a second lumen in combination with a filter separating the first and second lumens from one another, the filter being configured to permit fluids to pass therethrough while preventing the sampled tissue from passing therethrough.

20 Claims, 3 Drawing Sheets

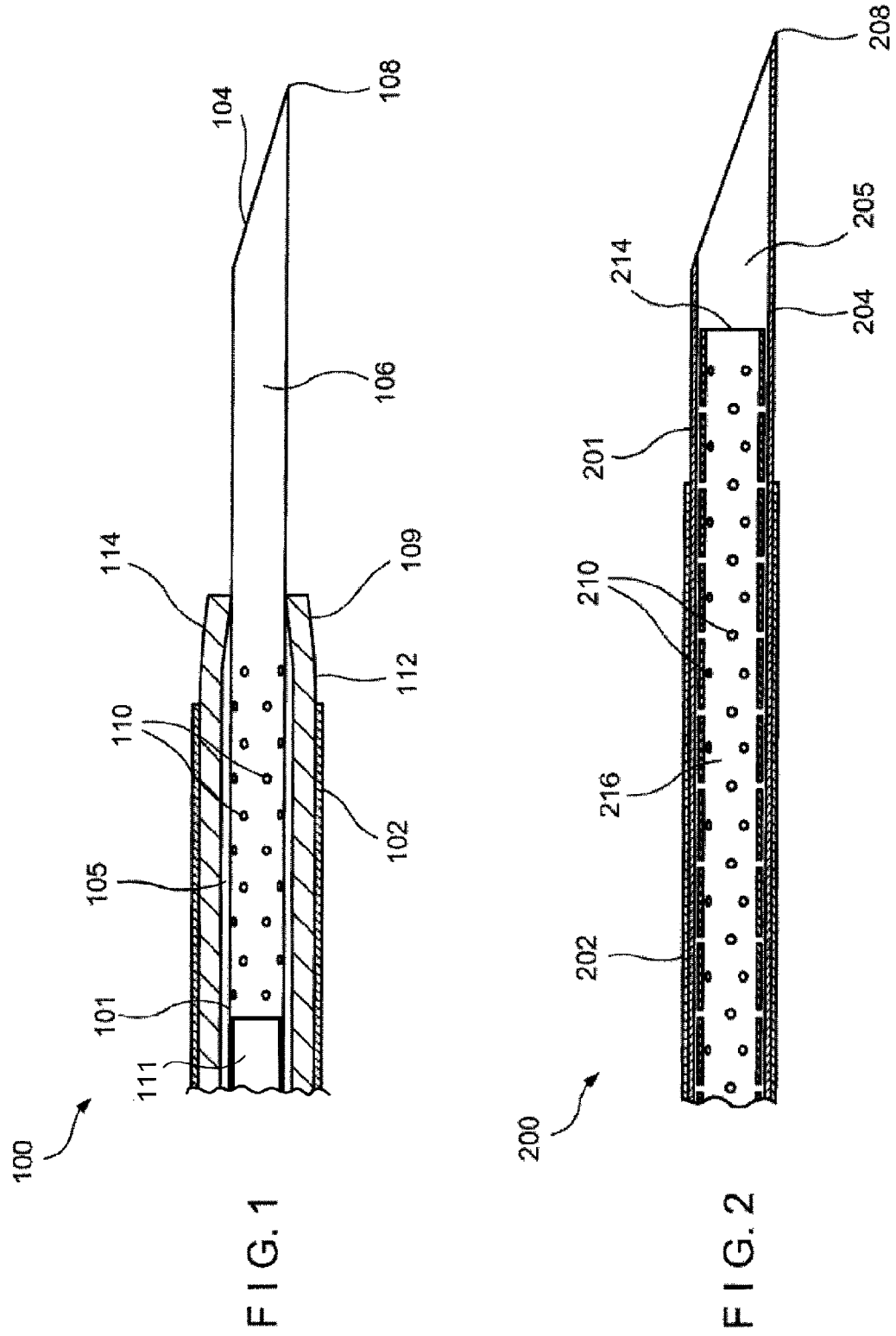

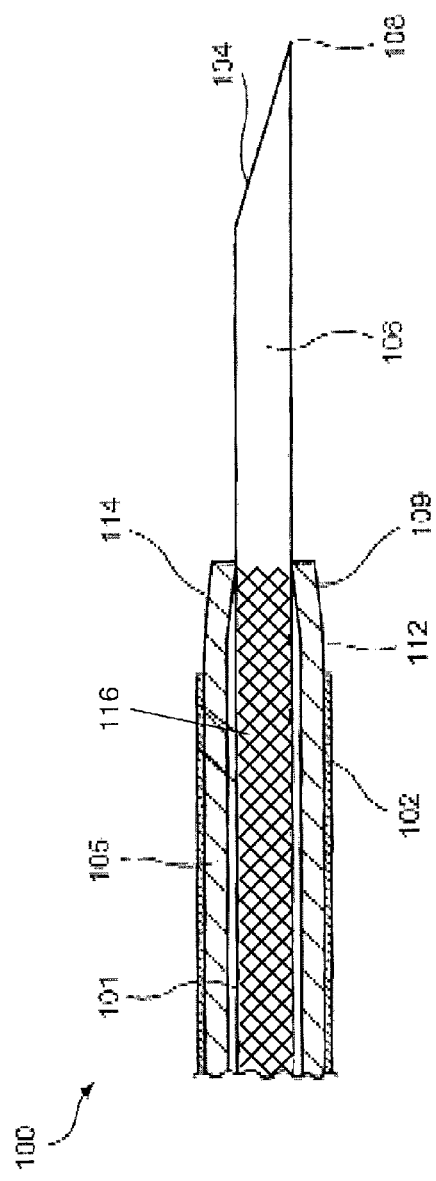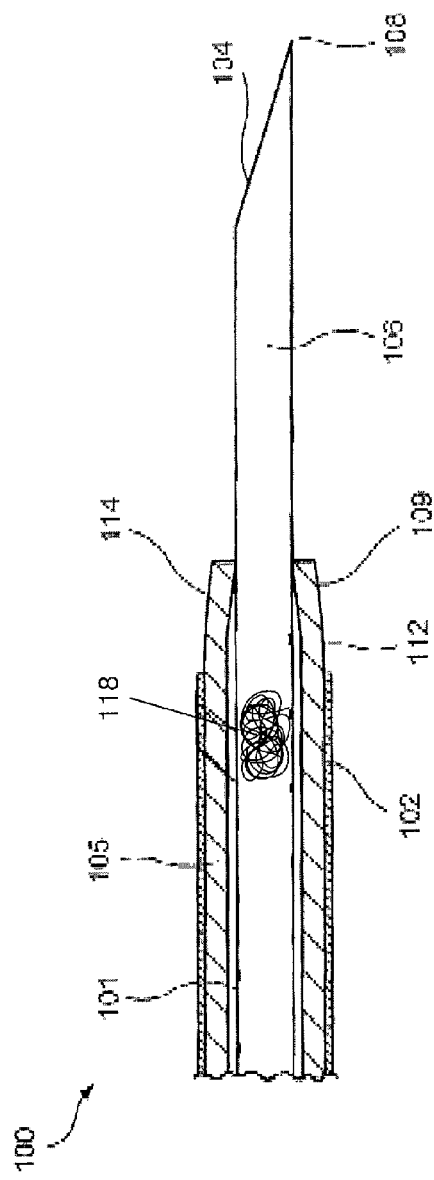

FILTER FOR FINE NEEDLE BIOPSY

PRIORITY CLAIM

The present application claims the priority to the U.S. Provisional Application Ser. No. 61/241,677, entitled "FILTER FOR FINE NEEDLE BIOPSY" filed on Sep. 11, 2009. The specification of the above-identified application is incorporated herewith by reference

BACKGROUND

Needle biopsies are often performed to diagnose and/or stage various pathologies. In these procedures, various size needles (i.e., 19 G, 22 G, 25 G) are often employed. However, these procedures are often inefficient in that the sampled biopsy material is obscured by unwanted matter (e.g., blood). Specifically, due to the increased trauma associated with puncturing tissue, an undesirable amount of blood may inadvertently be drawn into a needle diluting the sample and making it more difficult to analyze the sample.

SUMMARY OF THE INVENTION

The present invention is directed to a biopsy needle comprising a first lumen open to a tissue penetrating distal tip of the needle for receiving a tissue sample therein and a second lumen in combination with a filter separating the first and second lumens from one another, the filter being configured to permit fluids to pass therethrough while preventing the sampled tissue from passing therethrough.

BRIEF DESCRIPTION OF THE DRAWINGS

FIG. 1 shows a longitudinal cross-sectional view of a needle according to a first exemplary embodiment of the present invention;

FIG. 2 shows a longitudinal cross-sectional view of a needle according to a second exemplary embodiment of the present invention;

FIG. 3 shows a longitudinal cross-sectional view of a needle according to a third exemplary embodiment of the present invention;

FIG. 4 shows a longitudinal cross-sectional view of a needle according to a fourth exemplary embodiment of the present invention.

DETAILED DESCRIPTION

Figure 5:
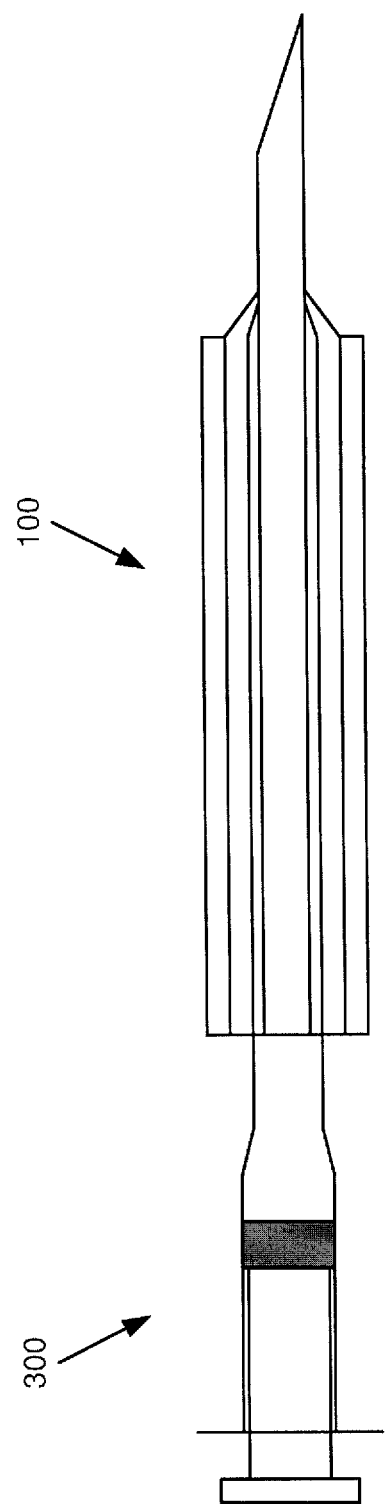
FIG. 5 shows a perspective view of a needle coupled to a syringe.

The present invention, which may be further understood with reference to the following description and the appended drawings, relates to devices for conducting biopsy procedures and in particular, to biopsy needles. Exemplary embodiments of the present invention provide a needle with a filtration mechanism to separate sampled target tissue from unwanted materials to obtain larger, undiluted samples.

An exemplary needle according to the present invention comprises an endoscopic ultrasound-guided fine-needle aspiration ("EUS-FNA") device for performing biopsy procedures on a living body. The needle of the present invention comprises two concentrically formed chambers separated from one another by a filter. The filter comprises a wall formed with multiple openings therein sized to allow cells of unwanted tissue to flow therethrough from one chamber to another while preventing the target tissue from passing between the chambers. Accordingly, target tissue brought into the needle according to any known method along with any unwanted material (e.g., blood) first enters a first chamber extending longitudinally through the needle. The blood drawn into the needle flows through the openings into the second chamber and is separated from the target tissue which can not pass through the filter.

As shown in FIG. 1, a device 100 according to an exemplary embodiment of the invention includes a needle 101 housed within a protective sheath 102 formed of any suitable biocompatible material as would be understood by those skilled in the art. The sheath 102 may, for example, be substantially rigid and includes a lumen sized and shaped to slidably receive the needle 101 therein. The needle 101 may be a 22 G needle as is commonly employed to obtain histological samples held within an outer tube 112 received within the sheath 102. The outer tube 112 is preferably 19 G and is separated from the needle 101 by an annular space 105 extending therearound. In a preferred embodiment, the needle gauge is within the range of 19 G-25 G, as known to those of skill in the art and, in one embodiment, may be selected such that a volume of the annular space 105 is greater than a volume of the needle 101 situated therein. In a preferred embodiment, the size of the annular space 105 is selected so that the acquired tissue sample is not compressed therewithin. It is noted, however, that this is not a requirement of the present invention and the annular space 105 may be formed with any dimensions without deviating from the scope of the present invention. The needle 101, which may be formed as a hypotube, includes a longitudinal body 106 extending from a proximal end (not shown) to a distal end comprising an open, puncturing tip 108 extending distally of a sealed distal end 114 of the outer tube 112. The proximal end (not shown) of the needle 101 further comprises a seal (e.g., a Touhy-Borst seal) configured to prevent the flow of air, fluids, etc. thereoutof. The seal permits a vacuum applied to the proximal end (not shown) to be transferred to the distal end of the needle 101. The seal (not shown) is also configured to permit advancement and retraction of a stylet 111 received through the needle 101, as described in greater detail hereinafter. In an alternate embodiment, the needle 101 does not extend through the full length of the sheath 102 but rather, only along a predetermined distal portion thereof. In one preferred embodiment, the needle 101 may extend approximately 0.305 meters from the distal end of the device 100. A proximal end of the needle 101 is then located a selected distance from the distal end and is operably connected to the stylet 111, which extends from the proximal end of the needle to a proximal end of the device 100 accessible to a user. In this embodiment, the stylet 111 is provided with a latching mechanism (not shown) that prevents the distal end of the stylet 111 from disengaging a proximal end of the needle 101. The latching mechanism (not shown) may be formed as a flattened portion on the stylet 111 configured to engage a protrusion formed on a proximal end of the needle 101, wherein engagement of the flattened portion with the protrusion prevents movement of the stylet 111 therepast. The protrusion may be formed around a periphery of the proximal end of the needle 101 so the rotation of the needle 101 does not dislodge the stylet 111 therefrom.

A lumen 104 extends through the needle 101 and a plurality of openings 110 formed along at least a portion of the longitudinal body 106 extend through a wall of the needle 101 to the lumen 104 providing for communication between the lumens 104 and 105. The openings 110 in this embodiment are formed along a substantially helical pattern, distributed evenly around a circumference of the longitudinal body 106.

It is noted however, that the openings 110 may be formed in any pattern or arrangement on the needle 101 without deviating from the scope of the present invention. For example, in an alternate embodiment (not shown), the openings 110 may be situated along only a portion of a circumference of the needle 101. The diameter of each of the openings 110 is selected to allow non-targeted materials to pass through while being too small to pass target tissue. For example, where the non-targeted material is blood, each opening 110 may have a diameter of approximately 8-10 μm allowing red blood cells to flow therethrough while preventing harvested target tissue from passing out. In an alternate embodiment, each of the openings 110 may comprise a diameter in the range of 1 μm.-250 μm to conform to the requirements of a target procedure. As the diameters of cell clusters of most tissue biopsies are greater than that of red blood cells, the openings 110 effectively function as a red blood cell filter, permitting only liquid and red blood cells to flow therepast into the lumen 105 while maintaining the target tissue in the lumen 104. The lumen 104 includes the stylet 111 therein which may be advanced into the open distal end 108 of the needle 101 to prevent foreign matter from entering the needle 101 during insertion. After the needle 101 has been advanced to the target site, the stylet 111 is withdrawn proximally into the needle 101 and the target tissue mass is penetrated to permit a target tissue sample to enter the lumen 104. Then, when the needle 101 has been withdrawn from the body, the stylet 111 may be advanced distally through the lumen 104 to eject the target tissue sample therefrom. It is further noted that the openings 110 are not restricted to circular apertures and may comprise any size and shape including, but not limited to, slits, slots, non-circular openings and any combination or pattern incorporating multiple sizes or shapes. Furthermore, the size of the openings may be chosen to accommodate the size of the cells to be filtered therethrough, as those skilled in the art will understand.

The outer tube 112 is seated within the protective sheath 102 and the distal end 114 thereof is sealed and tapered inward toward the needle 101. An end of the tapered distal end 114 is proximal with respect to the puncturing tip 108 of the needle 101 so that, when the distal tip 108 is pushed into target tissue, the larger diameter outer tube 112 may remain outside the target tissue mass reducing trauma thereto. Furthermore, the outer tube 112 is sized such that a frictional force between the outer tube 112 and the sheath 102 is minimized and, such that a small annular space lies therebetween in an operative configuration. It is noted that, although the present embodiment is described with a rounded tapered distal end 114, the distal end of the outer tube 112 may be formed of any shape including, but not limited to a square. Furthermore, the outer tube 112 may be attached to the needle 101 by any means known in the art such as adhesive bonding.

The needle 101 of the present invention may be used in a manner substantially similar to current procedures for the use of various EUS-FNA devices. Specifically, the device 100 is inserted into a living body via any known guiding apparatus as would be understood by those skilled in the art (e.g., under ultrasound guidance) until a distal portion thereof is adjacent to a target tissue mass to be sampled. As described above, during insertion the stylet (not shown) is advanced to a distalmost resting position with a distal end thereof seated in the opening at the distal tip 108 to prevent non-targeted tissue from entering the needle 101. When the target tissue portion has been reached, the stylet (not shown) is withdrawn proximally into the lumen 104 to create a space within which the tissue sample will be received. The needle 101 is then advanced distally into the target tissue driving target tissue into the distal end of the lumen 104. Specifically, the needle 101 is driven distally relative to the sheath 102 (e.g., by any known mechanism) to extend distally beyond the distal end 114 and penetrate the target tissue mass. As noted earlier, the portion of the needle 101 extending distally beyond the distal end 114 of outer tube 112 may be of any length depending on the requirements of a procedure to be performed. The sheath 102 may then be sized accordingly, so that, when retracted, the needle 101 is housed completely therein. Once the target tissue has been penetrated by the needle 101 and a sample of the target tissue has been forced into the distal end of the lumen 104, unwanted material is drawn out of the tissue sample by applying negative pressure to the lumen 105 (e.g., via a syringe 300 coupled to a proximal end thereof as illustrated in FIG. 5). This pressure draws the blood or other unwanted material through the holes 110 into the lumen 105 while the targeted sample of tissue is prevented from passing therethrough and remains in the lumen 104. After the sampling process has been completed, the device 100 is withdrawn proximally from the guiding device and removed from the body. The stylet (not shown) is once again advanced distally to eject the target biopsy material from the lumen 104 for analysis.

A device 200 according to an alternate embodiment of the invention includes a needle 201 including a substantially constant diameter outer body 202. The outer body 202 extends to an open, tissue penetrating distal tip 208 with a lumen 205 extending therethrough. It is noted that although the embodiment of FIG. 2 is shown with particular dimensions, the dimensions of the lumen 205 and the body 202 may be modified in any of a plurality of ways depending on the requirements of the procedures to be performed. The device 200 further includes a stylet 216 sized and shaped for slidable insertion through the lumen 205 so that a distal end of the stylet 216 may seal the distal opening to the lumen 205. When retracted proximally into the needle 201, the distal end of the stylet 216 is withdrawn into the lumen 205 so that sample tissue may enter the lumen 205.

As described above, during insertion of the needle 201 to a target tissue sampling site, the stylet 216 is advanced to a distalmost location in the lumen 205 to prevent unwanted tissue from entering the needle 201. An outer diameter of the stylet 216 is selected to be slightly less than an inner diameter of the lumen 205 so that it may be slidably received therein. The distal end of the stylet 216 is sealed so that, when in the distal-most position, the sealed distal end thereof prevents material from entering the lumen 205 via the opening in the distal tip 208. A plurality of openings 210 extend through the stylet 216, opening a lumen 214 extending therethrough to the lumen 205. As described in regard to the device 100 of FIG. 1, the openings 210 may be distributed substantially evenly around a circumference thereof (e.g., along a helical path) or in any desired pattern or distribution. Alternatively, the openings 210 may be placed in any desired positions along any desired path. As with the embodiment of FIG. 1, the openings 210 may comprise a diameter of approximately 8-10 μm. to allow red blood cells to pass therethrough while preventing the passage of target tissue.

When a target tissue area has been reached in the body, the stylet 216 is withdrawn proximally into the cavity 206 and the needle 201 is advanced distally (e.g., out of a guiding device) so that the puncturing tip 208 enters the target tissue. As would be understood by those skilled in the art, negative pressure may be transmitted through the stylet lumen 214 to the target tissue to aid in drawing target tissue into the lumen 205. It is noted that the stylet 216 is only partially retracted into the lumen 205, allowing enough clearance for a biopsy sample to enter therein without obstruction.

As with the device 100 of FIG. 1, the device 200 is advanced to a desired location adjacent to a target tissue mass to be sampled using any known means with the stylet 216 in the distal-most position to prevent the introduction of non-targeted tissue into the lumen 205. When the needle 204 has reached the desired position, the stylet 216 is withdrawn proximally into the lumen 205 to free a space therewithin to receive target tissue. The needle 204 is then inserted into the target tissue so that target tissue is forced into the lumen 205 via the opening in the distal tip 208. The user then reduces the pressure within the lumen 214 (e.g., via a vacuum source attached at the proximal end of the stylet lumen 214). This reduced pressure is communicated to the lumen 205 via the openings 210 and draws the contents of the lumen 205 toward the openings 210. As the openings 210 are sized to permit the passage of fluids such as blood therethrough while preventing passage of targeted tissue, the fluids are drawn into the lumen 214 while the target tissue remains within the lumen 205. If desired, the fluids may be withdrawn from the lumen 214 via a syringe (such as the syringe 300 of FIG. 5) or other mechanism as would be understood by those skilled in the art to prevent it from returning to the cavity 206 where it would dilute the target tissue sample. The device 200 is withdrawn from the body and the stylet 216 may be advanced distally to force the tissue sample out of the needle 204 via the opening in the distal tip 208.

In an alternate embodiment of the device of FIG. 2, a proximal portion of the stylet 216 may be tapered. In another alternate embodiment, the openings 210 may be replaced with a filter material placed at a distal tip of the stylet 216.

It will be apparent to those skilled in the art that various modifications and variations may be made to the structure and methodology of the present invention without departing from the spirit or scope of the invention. For example, the exemplary needle of the present invention may be formed with any of various tip grinds. Furthermore, the filtering of fluid through the exemplary embodiment of the present invention need not be limited to openings in the hypotube and may include a filtering medium (e.g., a non-woven fiber plug) situated on the needle to assist in filtering. The filtering medium can be situated similar to the openings of FIGS. 1 and 2 or, in an alternate embodiment, may be placed over a distal opening of the needle, as those skilled in the art will understand. For example, as shown in FIG. 3, the filtering medium may be a membrane 116 extending along a portion of the longitudinal body 106 housed within the large diameter outer tube 112. In another example, as shown in FIG. 4, the filtering medium may be a plug 118 disposed within the lumen 104 of the longitudinal body 106. Still further, the annular space 105 or cavity 206 that receives the unwanted tissue and other matter, can assume any shape known in the art and is not limited to symmetrical embodiments. Thus, the present invention covers all modifications and variations so as they come within the scope of the appended claims and their equivalents.

What is claimed is:

1. A biopsy needle, comprising:
    a longitudinal body including a first lumen open to a tissue penetrating distal tip at a distal end of the longitudinal body for receiving a tissue sample therein;
    an outer tube slidably receiving the longitudinal body within a second lumen extending through the outer tube, the second lumen being sized to form a space between an inner surface of the outer tube and an outer surface of the longitudinal body; and
    a filter separating the first lumen from the space, the filter being configured to permit fluids to pass therethrough from the first lumen into the space while preventing the sampled tissue from passing therethrough.

2. The biopsy needle according to claim 1, wherein the filter has an opening formed on a wall of the longitudinal body.

3. The biopsy needle according to claim 2, wherein the opening is between approximately 1 μm and 250 μm in diameter.

4. The biopsy needle according to claim 1, wherein a cross-sectional shape of the first and second lumens is symmetrical.

5. The biopsy needle according to claim 4, wherein the second lumen surrounds the first lumen.

6. The biopsy needle according to claim 4, wherein a distal end of the second lumen forms a seal about the longitudinal body and a proximal end of the second lumen includes a proximal port coupleable to a source of negative pressure to aspirate fluids therefrom, the seal facilitating the withdrawal of fluid from the first lumen into the space via the application of suction to the second lumen.

7. The biopsy needle according to claim 1, further comprising:
    a stylet slidably received within the first lumen.

8. The biopsy needle according to claim 7, wherein the second lumen extends through the stylet, the filter being formed as an opening in the stylet opening the second lumen to an exterior of the stylet.

9. The biopsy needle according to claim 7, wherein the proximal end of the second lumen is coupleable to a vacuum source to lower a pressure within the second lumen and draw fluids from the first lumen into the second lumen.

10. The biopsy needle according to claim 1, wherein the filter comprises a plurality of openings sized to permit only predetermined particulate matter therethrough.

11. The biopsy needle according to claim 10, wherein the openings are sized to permit red blood cells to pass therethrough but are sized to prevent cells of target tissue from passing therethrough.

12. The biopsy needle according to claim 11, wherein the openings are less than approximately 10 μm in diameter.

13. The biopsy needle according to claim 12, wherein the openings are greater than approximately 8 μm in diameter.

14. The biopsy needle according to claim 10, wherein the openings are distributed over at least a portion of the longitudinal body in a substantially helical pattern.

15. The biopsy needle according to claim 1, wherein the second lumen surrounds the first lumen with the filter formed as a series of openings in a wall of the longitudinal body.

16. The biopsy needle according to claim 2, wherein the filter is a membrane.

17. The biopsy needle according to claim 2, wherein the filter is a plug.

18. A method for performing a needle biopsy, comprising:
    advancing a needle into a target portion of tissue to capture a sample of the target tissue within a first lumen of a longitudinal body of the needle; and
    reducing a pressure within a second lumen of an outer tube of the needle, the outer tube slidably receiving the longitudinal body within the second lumen, the second lumen being sized to form a space between an inner surface of the outer tube and an outer surface of the longitudinal body such that fluids are drawn from the sampled tissue through a filter separating the first lumen from the space, the filter preventing passage into the space of the sampled target tissue while permitting fluids to pass therethrough from the first lumen into the space.

19. The method of claim 18, wherein the second lumen extends within a stylet slidably received within the first lumen, the filter comprising a plurality of openings in the stylet.

20. The device of claim 9, wherein the vacuum source is a syringe.

* * * * *